United States Patent
Lukoschek et al.

(10) Patent No.: US 10,456,058 B2
(45) Date of Patent: Oct. 29, 2019

(54) SENSOR DEVICE OR EEG ELECTRODE AND CAP HAVING A PLURALITY OF SENSOR DEVICES

(71) Applicant: BRAIN PRODUCTS GMBH, Gilching (DE)

(72) Inventors: Peter Lukoschek, Haidmuehle (DE); Johann Strasser, Obermeitingen (DE); Manfred Jaschke, Munich (DE)

(73) Assignee: Brian Products GmbH, Gilching (DE)

( * ) Notice: Subject to any disclaimer, the term of this patent is extended or adjusted under 35 U.S.C. 154(b) by 266 days.

(21) Appl. No.: 15/332,087

(22) Filed: Oct. 24, 2016

(65) Prior Publication Data

US 2017/0224278 A1 Aug. 10, 2017

(30) Foreign Application Priority Data

Feb. 10, 2016 (DE) .................. 20 2016 100 667 U

(51) Int. Cl.
*A61B 5/0478* (2006.01)
*A61B 5/00* (2006.01)

(52) U.S. Cl.
CPC .......... *A61B 5/0478* (2013.01); *A61B 5/6803* (2013.01); *A61B 5/6843* (2013.01); *A61B 5/6814* (2013.01); *A61B 5/6831* (2013.01); *A61B 2562/164* (2013.01)

(58) Field of Classification Search
CPC ........................... A61B 5/0478; A61B 5/6803
USPC ................................................ 600/383, 544
See application file for complete search history.

(56) References Cited

U.S. PATENT DOCUMENTS

| 2,409,033 | A | * | 10/1946 | Garceau | A61B 5/0476 330/120 |
| 4,770,180 | A | * | 9/1988 | Schmidt | A61B 5/0478 600/383 |
| 6,574,513 | B1 | | 6/2003 | Collura et al. | |
| 9,398,864 | B2 | * | 7/2016 | Lawrence | A61B 5/0478 |
| 2008/0306397 | A1 | | 12/2008 | Bonmassar et al. | |
| 2012/0143020 | A1 | | 6/2012 | Bordoley et al. | |
| 2015/0257673 | A1 | | 9/2015 | Lawrence et al. | |
| 2016/0022165 | A1 | * | 1/2016 | Sackellares | A61B 5/0478 600/383 |
| 2016/0066804 | A1 | * | 3/2016 | Peuscher | A61B 5/0478 600/383 |

FOREIGN PATENT DOCUMENTS

| WO | WO2012/105493 | * | 8/2012 | A61B 5/0478 |
| WO | WO2013/080992 | * | 6/2013 | A61B 5/0478 |

* cited by examiner

*Primary Examiner* — Lee S Cohen
(74) *Attorney, Agent, or Firm* — Laurence A. Greenberg; Werner H. Stemer; Ralph E. Locher

(57) ABSTRACT

A sensor device which is suitable for receiving and transmitting signals and can be placed on a test person's head, includes a sensor device housing having a signal pin on its distal side for receiving a signal and a connection on its proximal side for the signal transmission of a signal received by the signal pin. A sensor device holder has an axial through opening in which the sensor device housing is disposed so as to be steplessly axially displaceable. When the sensor device housing is axially displaced relative to the sensor device holder, the sensor device housing does not change its radial orientation. A cap having a plurality of sensor devices is also provided.

11 Claims, 10 Drawing Sheets

A-A

US 10,456,058 B2

SENSOR DEVICE OR EEG ELECTRODE AND CAP HAVING A PLURALITY OF SENSOR DEVICES

CROSS-REFERENCE TO RELATED APPLICATION

This application claims the priority, under 35 U.S.C. § 119, of German Patent Application DE 20 2016 100 667.8, filed Feb. 10, 2016; the prior application is herewith incorporated by reference in its entirety.

BACKGROUND OF THE INVENTION

Field of the Invention

The invention relates to a sensor device which is suitable for receiving and transmitting signals and can be placed on a test person's head. Further, the invention relates to an EEG electrode which is suitable for receiving and transmitting EEG signals and can be placed on a test person's head. The invention also relates to a cap having a plurality of sensor devices.

Electrodes which are placed on the human skin at a measuring point and are connected to a measuring apparatus (amplifier) by using an electric cable are used for acquiring (deriving) electrophysiological signals (e.g. EEG, EOG, ECG, EMG, etc.).

Such EEG electrodes are placed on a test person's head for the acquisition of an EEG (electroencephalogram), for example. EEG signals acquired by the electrodes are entered from the EEG electrode into the measuring apparatus through cables for further processing.

Such EEG recordings are carried out, for instance, in laboratories or during a magnetic resonance scan or a computer tomography scan.

U.S. Patent Application US 2008/0306397 A1 discloses a cap adapted to be placed on the head of a test person. A plurality of electrodes each including a sensor is attached to the cap. In practical use the cap is placed on the test person's scalp in such a manner that, ideally, the sensors abut the scalp of the test person. For that purpose, the sensors are provided with an appropriate paste, a so-called EEG paste. The end portion of the sensors, provided with paste, then abuts the test person's scalp.

Usually, a gel, a paste or an electrolyte is used to improve (i.e. minimize) the contact resistance between the electrode and the human skin. The disadvantage of gels and pastes is that gel residues remain at the derivation location after the derivation is finished. If there is hair at the derivation location, it sticks together due to those residues. In particular, in the case of EEG derivations from the scalp and derivations including many electrodes it is thus usually necessary to wash the hair after the derivation, which increases the total duration of the treatment and constitutes an additional burden or inconvenience for test persons/patients. Therefore, attempts to develop electrodes that can be used without gel/pastes (so-called dry electrodes) have already been made for many years. Some manufacturers offer such dry electrodes commercially (see e.g. http://www.gtec.at/Products/Electrodes-and-Sensors/g.SAHARA-Specs-Features and http://www.brainproducts.com/product-details.php?id=56).

Due to different sizes and shapes of heads, it is required that all kinds of electrodes (not only dry electrodes) be fixed in different ways near the derivation location. In many cases that object is achieved by using elastic or plastic materials (so-called electrode caps or nets), using mechanical springs or adjustable pulling mechanisms.

In order to achieve a high signal quality, an even better mechanical contact to the derivation location (e.g. a higher contact pressure) is particularly required for dry electrodes in comparison to electrodes used in combination with gels, pastes or electrolytes. Thus, due to the different sizes and shapes of heads, the aim is to provide a mechanism that makes it possible to establish a stable mechanical and consequently electrical contact between the dry electrode and the scalp at any location on the head and for any size and shape of the head. In that case, it is difficult to achieve a balance between a sufficient contact pressure and the individual sensation of pain.

If, in the application of dry electrodes, no paste or gel, etc. is used between the sensors of the electrodes and the test person's scalp, the signal-acquiring sensor ends should ideally abut directly against the test person's scalp. Sensors of different lengths can be used so as to ensure a safe abutment of the sensors against the test person's scalp. More precisely, a sensor that is too far away from the test person's scalp for a contact to be established, can be replaced by a sensor with an appropriately greater length. Hence, a cap having electrode sensors can be used, with the cap being adjustable to the individual head shape of the respective test person by choosing electrode sensors of an appropriate length at every position of the cap where electrode sensors are disposed.

However, such a cap is usually adjusted to the respective test person by the treating person. If, in the course of a treatment, an electrode sensor exerts too much pressure on the test person's scalp, that may cause the test person to feel severe pain. Then, the treating person must replace the respective electrode sensor by a more appropriate one. Since the test person does not perform the above-explained adjustment himself or herself, that procedure is complicated and cumbersome.

SUMMARY OF THE INVENTION

It is accordingly an object of the invention to provide an improved sensor device or EEG electrode and a cap having a plurality of sensor devices, which overcome the hereinafore-mentioned disadvantages of the heretofore-known devices of this general type and which can be better adjusted to individual circumstances when used on the skin of a test person.

With the foregoing and other objects in view there is provided, in accordance with the invention, a sensor device suitable for receiving and transmitting signals and for placement on a test person's head. The sensor device comprises a sensor device holder having an axial through opening, a sensor device housing disposed in the axial through opening so as to be steplessly axially displaceable, the sensor device housing having a distal side and a proximal side, the sensor device housing having a radial orientation being maintained upon the sensor device housing being axially displaced relative to the sensor device holder, a signal pin disposed on the distal side of the sensor device housing for receiving a signal, and a connection disposed on the proximal side of the sensor device housing for signal transmission of a signal received by the signal pin.

With the objects of the invention in view, there is also provided a cap, comprising a plurality of sensor devices according to the invention. The sensor device holder of each respective sensor device is disposed in a respective predefined opening in the cap, permitting the sensor device housing to be operated from a side of the cap opposite to the signal pins for a stepless axial displacement of the sensor device housing relative to the sensor device holder.

Advantageous further developments are the subject matter of the dependent claims.

Thus, in the present invention, a sensor device is realized by a stepless screw mechanism which can be adjusted by the test person himself or herself as well as by the treating person and which, for instance, can also be combined with sensors of different length (stages).

Other features which are considered as characteristic for the invention are set forth in the appended claims.

Although the invention is illustrated and described herein as embodied in a sensor device or EEG electrode and a cap having a plurality of sensor devices, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1A:
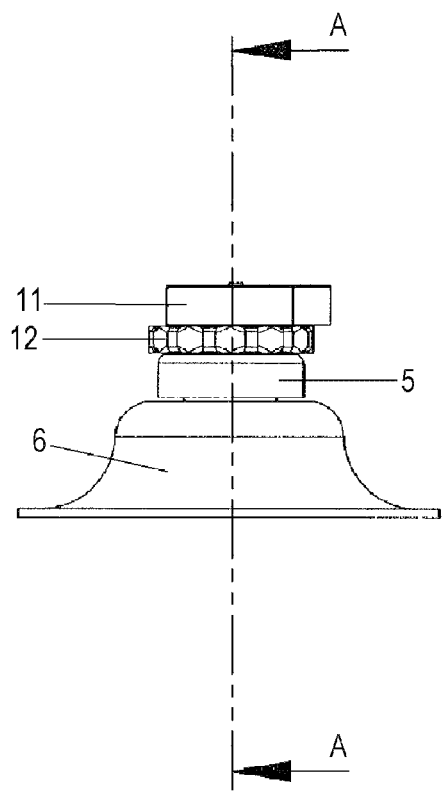
FIG. 1A shows a side view of an EEG electrode according to an embodiment of the invention.

Referring now to the figures of the drawings in detail and first, particularly, to FIGS. 1A-1F and FIGS. 2A-2E thereof, there is seen an EEG electrode of the embodiment in an assembled state.

The EEG electrode according to the invention is suitable for receiving and transmitting EEG signals and can be placed on a test person's head for this purpose.

The EEG electrode according to the invention is formed of an electrode housing 11 including an electrode 2, 4, an electrode holder upper part 12 and an electrode holder bottom part 13. The electrode housing 11, the electrode holder upper part 12 and the electrode holder bottom part 13 are made of resin, for example. The electrode holder upper part 12 and the electrode holder bottom part 13 form the electrode holder 12, 13 into which the electrode housing 11 is screwed. An electrode pin 2 for receiving an EEG signal is disposed on the distal side in the electrode housing 11, i.e. on the side facing toward a test person, wherein a sensor 4 is plugged onto the electrode pin 2. A connection 3 for the signal transmission of a signal received by the electrode pin 2 is disposed on the proximal side of the electrode housing 11. Through the use of a ring 5, the electrode holder 12, 13 is attached to a cap 6 which can be put on the test person's head.

The individual parts of the EEG electrode according to the invention are explained below through the use of the drawings.

Electrode Housing 11:

The electrode housing 11 is shown in detail in FIGS. 3A-3F.

Figure 1B:
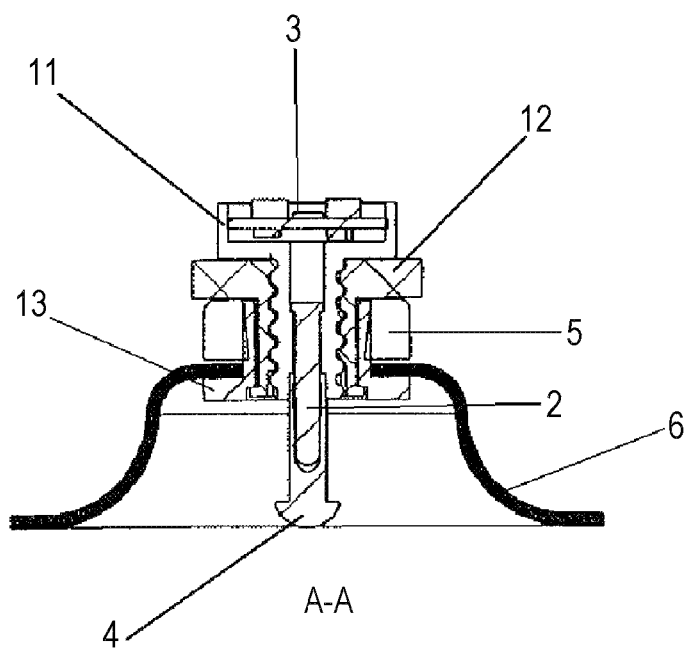
FIG. 1B shows a sectional view of the EEG electrode of FIG. 1A along the line A-A.

As is seen in FIG. 1B, the electrode housing 11 has an electrode pin 2 on its distal side for receiving an EEG signal and a connection 3 on its proximal side for the signal transmission of a signal from the electrode pin 2. The electrode pin 2 and the connection 3 are electrically connected in the electrode housing 11, so that a signal received by the electrode pin 2 can be transmitted by the connection 3.

Figure 3A:
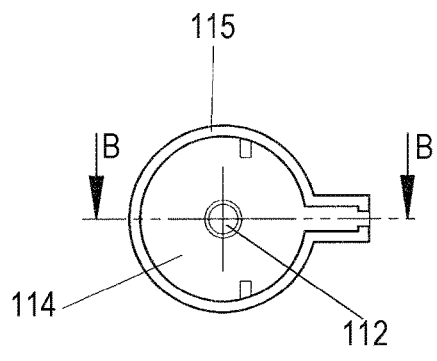
FIG. 3A shows a top view on an electrode housing of the EEG electrode of the embodiment of the invention.
Figure 3B:
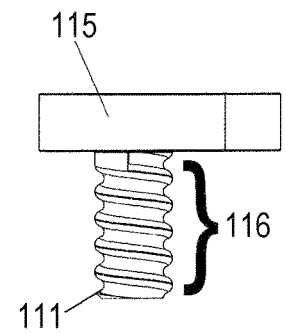
FIG. 3B shows a side view of the electrode housing.
Figure 3C:
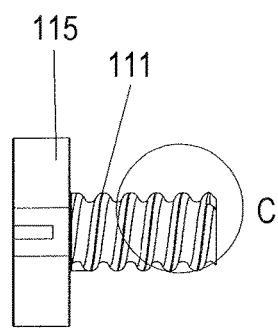
FIG. 3C shows another side view of the electrode housing.
Figure 3D:
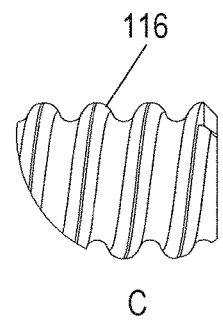
FIG. 3D shows a detail C of FIG. 3C.
Figure 3E:
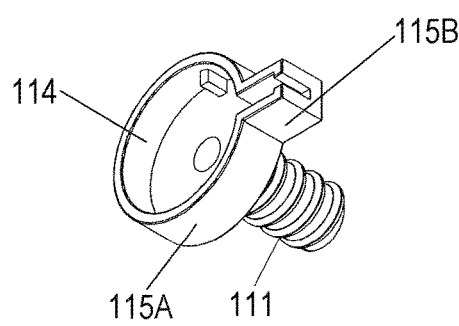
FIG. 3E shows a perspective view of the electrode housing.

As is shown in FIG. 3E, the electrode housing 11 has a flat head 115, on the distal side of which a cylindrical extension 111 is disposed. The flat head 115 is formed as a bottomed flat cylinder 115A on the outer circumference of which a protrusion 115B projects integrally. Both the bottomed flat cylinder 115A and the protrusion 115B have on their outer circumference a wall extending in the proximal direction which, together with the bottom of the cylinder 115A and the bottom of the protrusion 115B, defines a space 114, i.e. a housing for placement of the connection 3. The protrusion 115B has an opening on the radially outer side from which the connection 3 projects radially outward to achieve a signal transmission to a measuring apparatus through a cable, for instance.

Figure 1C:
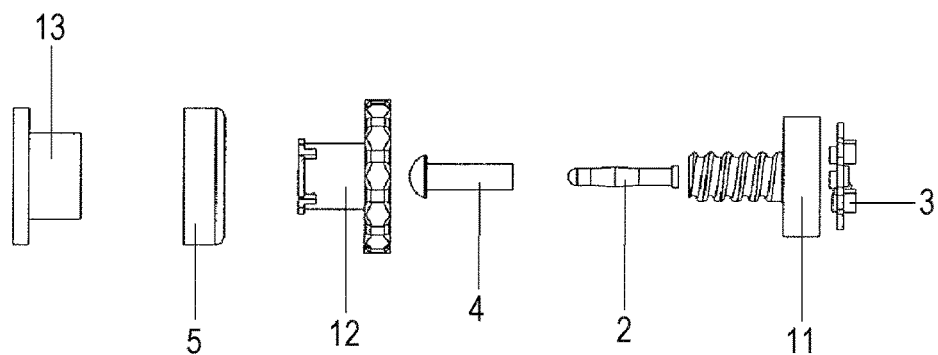
FIG. 1C shows an exploded view of the EEG electrode.
Figure 1D:
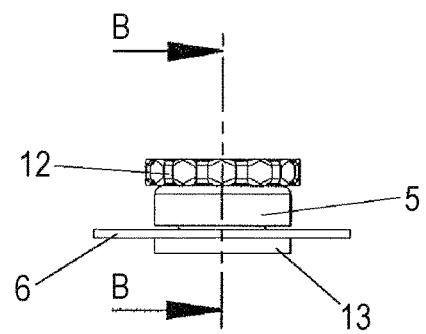
FIG. 1D shows a side view of the EEG electrode, the electrode housing being omitted.
Figure 2A:
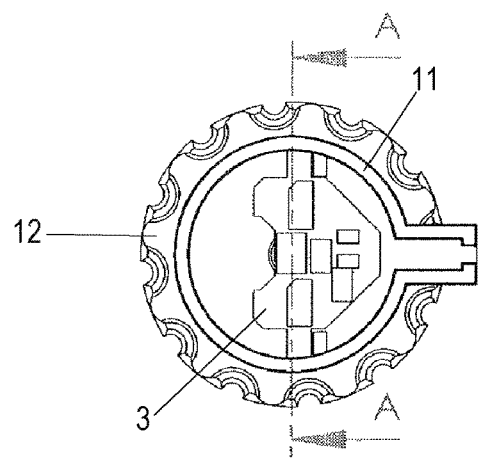
FIG. 2A shows a top view on an EEG electrode according to an embodiment of the invention.

The connection 3 is formed as a circuit board in the embodiment, as shown in FIGS. 1C and 2A. Alternatively, the connection 3 can be formed as simple conductor. Further, the connection 3 can be formed as a circuit board with an amplifier and/or a preamplifier and/or an A/D converter. The connection 3 is inserted into and anchored in the space 114 from the proximal side for placement of the connection 3. The connection 3 can be glued in the space 114 and/or can be held there in a form-locking manner.

Figure 3F:
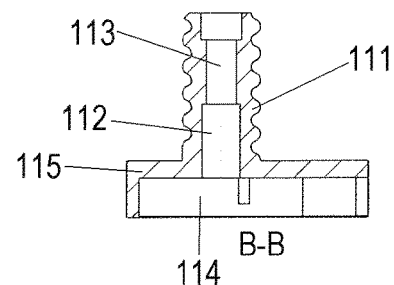
FIG. 3F shows a sectional view of the electrode housing along the line B-B in FIG. 3A.

The cylindrical extension 111 extends on the side opposite to the wall of the cylinder 115A, i.e. the distal side of the head 115. The central axis of the cylindrical extension 111 forms an elongation of the central axis of the cylinder 115A, as is seen in FIGS. 3C and 3E. A through bore 112 is formed in the bottom of the cylinder 115A and on the inside of the extension 111, as is seen in FIG. 3F. The through bore 112 is used for accommodating the electrode pin 2.

The through bore 112 has a portion 113 having a reduced inner diameter. The electrode pin 2 can be held at the inner circumference of the portion 113 having a reduced inner diameter, as is seen in FIG. 1B. The distal end of the portion 113 having a reduced inner diameter may serve as a stop for the sensor 4 placed on the electrode pin 2.

As is shown in FIGS. 3B-3D, the cylindrical extension 111 has a male thread 116 formed as left-hand thread in the embodiment. Through the use of the male thread 116 the electrode housing 11 is steplessly displaceable relative to the electrode holder 12, 13 by using a screwing movement.

The electrode holder upper part 12 and the electrode holder bottom part 13 together form the electrode holder.

Electrode Holder Upper Part 12:

The electrode holder upper part 12 is shown in detail in FIGS. 4A-4F.

The electrode holder upper part 12 is formed of a cylindrical body 123 having a wheel body 122 on its front side. The outer diameter of the wheel body 122 is larger than the outer diameter of the cylindrical body 123. The cylindrical body 123 and the wheel body 122 are formed integrally or in one piece and have the same center axis. A through opening 121 is provided along the center axis of the cylindrical body 123 and the wheel body 122. A female thread 125 formed as left-hand thread in the embodiment is formed in the through opening 121. The male thread 116 of the electrode housing 11 is in threaded engagement in the female thread 125. Thus, the thread parameters of the female thread 125 are selected in accordance with the male thread 116 of the electrode housing 11 (appropriate lead and pitch, etc.).

Figure 4A:
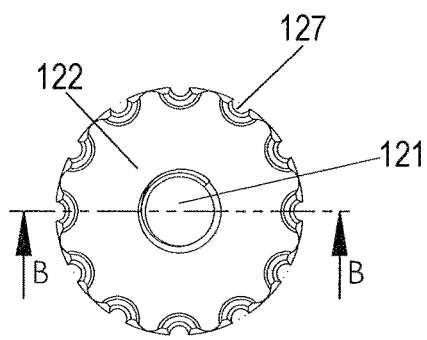
FIG. 4A shows a top view of an electrode holder upper part of the EEG electrode of the embodiment of the invention.
Figure 4B:
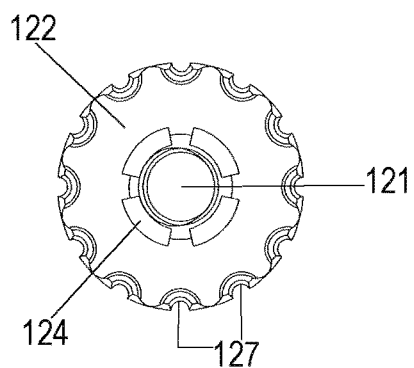
FIG. 4B shows a bottom view of the electrode holder upper part.
Figure 4C:
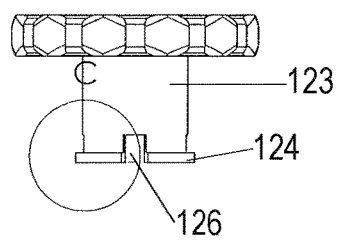
FIG. 4C shows a side view of the electrode holder upper part.
Figure 4D:
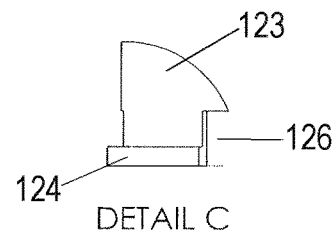
FIG. 4D shows a detail C of FIG. 4C.
Figure 4E:
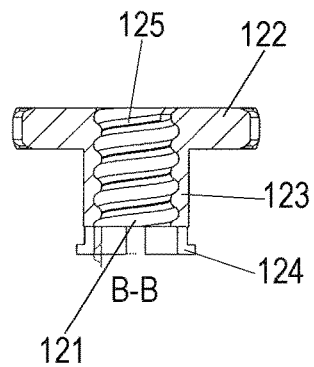
FIG. 4E shows a sectional view of the electrode holder upper part along the line B-B in FIG. 4A.
Figure 4F:
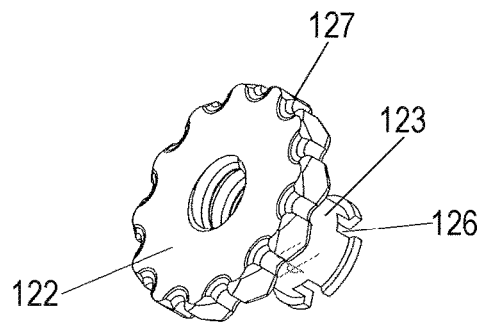
FIG. 4F shows a perspective view of the electrode holder upper part.

The wheel body 122 has a knurl 127 on the outer circumferential surface, as is seen in FIGS. 4A, 4B and 4F. The knurl 127 is made up of recesses and projections on the outer circumference or periphery or circumferential surface. The recesses can be spaced apart from each other on the circumference at a predetermined angle, as is seen in FIG. 4A. The knurl 127 can be arbitrarily constructed so as to enable a test person to advantageously grip and turn the electrode holder upper part 12.

The cylindrical body 123 has a radially outwardly projecting flange 124 on its outer circumference on the side opposite to the wheel body 122. Moreover, the cylindrical body 123 has at least one groove 126 (in the present embodiment: four) on the side opposite to the wheel body 122. The groove 126 extends axially parallel to the center axis of the electrode holder upper part 12, as is seen in FIGS. 4C-4F. The groove 126 has an axial length which, in the axial direction of the electrode holder upper part 12, is greater than the thickness of the flange 124. If multiple grooves 126 are applied, they are preferably disposed so as to be equally spaced along the circumference at the end of the cylindrical body 123, as is seen in FIG. 4F. The grooves 126 have the effect that the end of the cylindrical body 123, provided with the flange 124, can be pushed inwards so as to insert the electrode holder upper part 12 into the electrode holder bottom part 13.

Electrode Holder Bottom Part 13:

The electrode holder bottom part 13 is shown in detail in FIGS. 5A-5D.

Figure 5A:
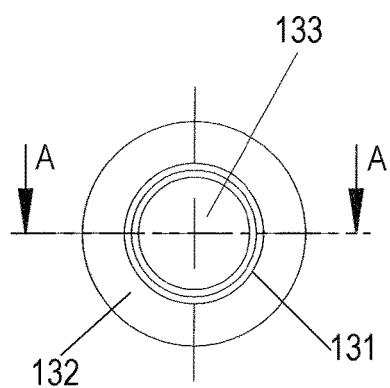
FIG. 5A shows a top view of an electrode holder bottom part of the EEG electrode of the embodiment of the invention.
Figure 5B:
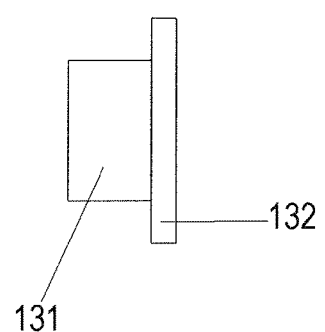
FIG. 5B shows a side view of the electrode holder bottom part.
Figure 5C:
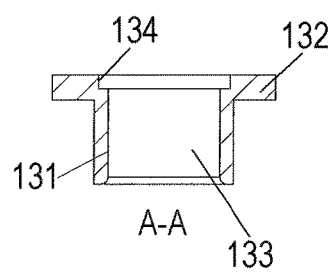
FIG. 5C shows a sectional view of the electrode holder bottom part along the line A-A in FIG. 5A.
Figure 5D:
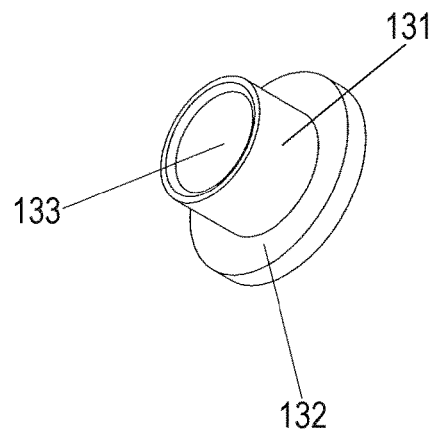
FIG. 5D shows a perspective view of the electrode holder bottom part.

The electrode holder bottom part 13 is formed by a cylinder sleeve 131, on the front side of which an annular flange 132 is formed integrally or in one piece, as is shown in FIG. 5C. The outer circumferential surface of the cylinder sleeve 131 serves for placement of the EEG electrode in a configuration hole formed in the cap 6, as is seen in FIG. 1B.

The cylinder sleeve 131 and the annular flange 132 have a common center axis. A through hole 133 extends along the center axis through the cylinder sleeve 131 and the annular flange 132, as is shown in FIG. 5C. The inner diameter of the through hole 133 is larger than an outer diameter of the cylinder body 123 of the electrode holder upper part 12. A step-shaped recess 134 having an inner diameter larger than the inner diameter of the through hole 133 is formed in the through hole 133 on the end side of the through hole 133 in the annular flange 132, opposite to the cylinder sleeve 131.

The through hole 133 has a rounded portion on its inner circumference on the side opposite to the annular flange 132, so as to facilitate an insertion of the electrode holder upper part 12.

Figure 2B:
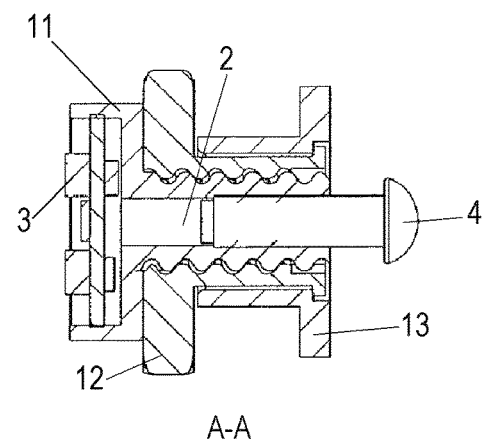
FIG. 2B shows a sectional view of the EEG electrode along the line A-A in FIG. 2A.
Figure 2C:
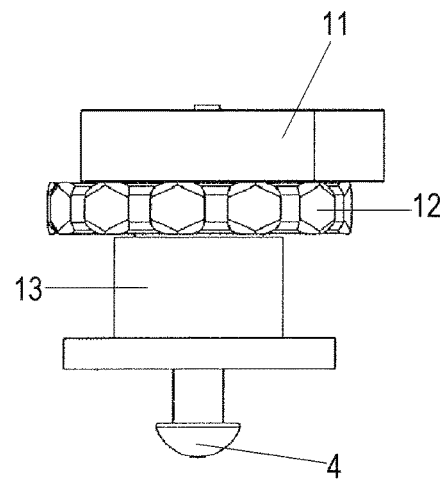
FIG. 2C shows a side view of the EEG electrode of FIG. 2A.

The electrode holder 12, 13 is assembled by pressing the flange of the electrode holder upper part 12 inwards and by pushing the electrode holder upper part 12 into the electrode holder bottom part 13 so that the flange side of the electrode holder upper part 12 with compressed flange portions 124 is inserted into the through hole 133 of the cylinder sleeve on the side opposite to the annular flange 132 and is pushed through the through hole 133 until the flanges 124 reach the recess 134 on the opposite side of the through hole 133. Once they have reached the recess 134, the compressed flanges 124 are relieved due to the greater diameter of the recess 134 as compared to the smaller inner diameter of the through hole 133, they move radially outward and they snap into place at the recess 134. This state, in which the electrode holder upper part 12 is disposed in the electrode holder bottom part 13 and the flange 124 snaps into place in the recess 134, is shown in FIG. 2B.

Thus, the electrode holder upper part 12 is rotatable relative to the electrode holder bottom part 13 while the cylinder sleeve 131 slides on the cylinder body 123 as a slide bearing.

Figure 6A:
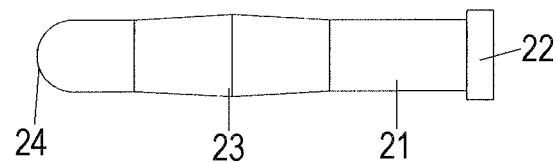
FIG. 6A shows a side view of an electrode pin of the EEG electrode of the embodiment of the invention.
Figure 6B:
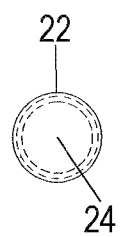
FIG. 6B shows a top view of the electrode pin.
Figure 6C:
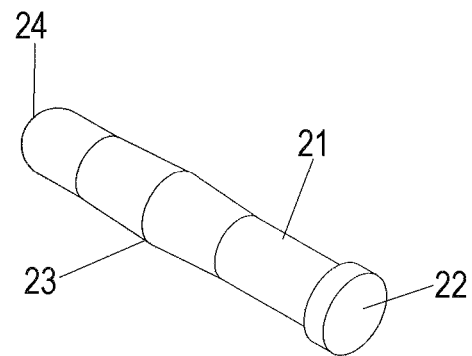
FIG. 6C shows a perspective view of the electrode pin.

Electrode Pin 2:

FIGS. 6A to 6C show the electrode pin 2 in detail. The electrode pin 2 is made of an electrically conductive material. The electrode pin 2 can be formed as a known so-called multilam plug or lamellar plug. The electrode plug 2 includes a shaft 21 on the end of which a head 22 is disposed so that an almost nail-like structure is achieved. The head 22 has a greater outer diameter than the shaft 21. The shaft 21 is formed so as to be cylinder-shaped and has an extended diameter portion 23 centrally along its longitudinal direction, for example, as is shown in FIGS. 6A and 6C.

The shaft 21 has a rounded end 24 at its end opposite to the head 22.

The increased diameter portion 23 is formed on the electrode pin 2 by lamella pin-shaped leaf spring contacts known from the prior art, forming lined-up ridges (not shown in the drawings) disposed in the circumferential direction of the shaft 21. These ridges provided as leaf spring contacts are used for realizing respective predefined contact points to an inner circumferential surface of the subsequently explained sensor 4.

The increased diameter portion 23 on the shaft 21 is chosen in such a way that the shaft 21 can be pushed through the small inner diameter portion 113 of the through hole 112. In other words, the outer diameter on the increased diameter portion 23 is of the same size or smaller than the inner diameter of the portion 113. The electrode pin 2 is inserted into the electrode housing 11 so that it is inserted with the rounded end 24 into the through hole 112 from the proximal side of the electrode housing 11. The electrode pin 2 is pushed into the through bore 112 of the electrode housing 11 until the head 22 abuts against the proximal end of the through bore 112. In this state, the end portion of the electrode pin 2, provided with the rounded end 24, projects from the distal side of the electrode housing 11.

Figure 7A:
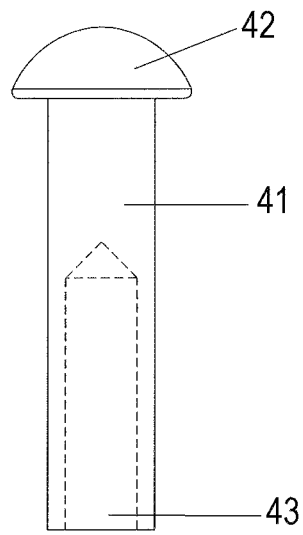
FIG. 7A shows a side view of a sensor of the EEG electrode of the embodiment of the invention.
Figure 7B:
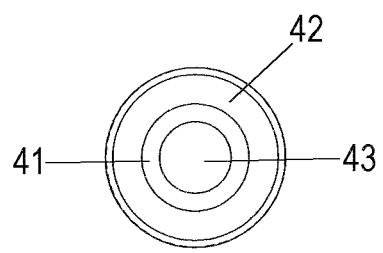
FIG. 7B shows a top view of the sensor.
Figure 7C:
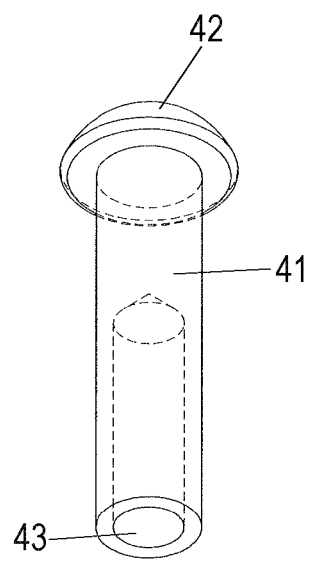
FIG. 7C shows a perspective view of the sensor.
Figure 8:
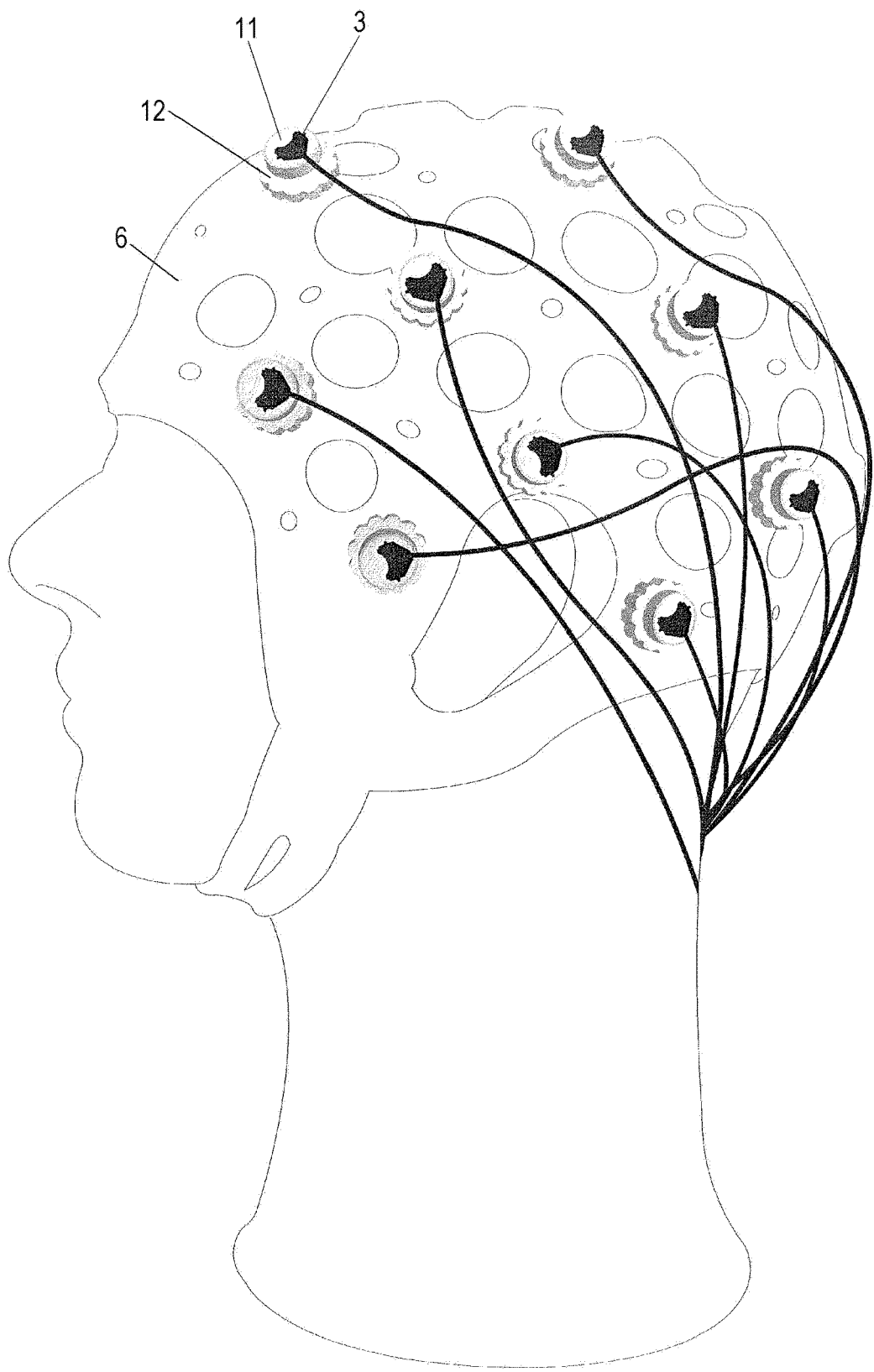
FIG. 8 shows a cap according to the invention, including the EEG electrode of the embodiment of the invention.

Sensor 4:

FIGS. 7A to 7C show the sensor 4 of the present embodiment.

The sensor 4 is made of an electrically conductive material. The sensor 4 includes a sensor shaft 41 at the end of which a sensor head 42 is formed. The sensor head has a greater outer diameter than the sensor shaft. The sensor head 42 has a rounded portion on the side facing away from the sensor shaft 41, as is shown in FIG. 7A. The rounded portion of the sensor head 42 serves as a contact surface of a dry electrode for a contact with the test person's skin. The rounded shape of the sensor head 42 has the effect that a contact of the sensor head 42 with the skin is not perceived as unpleasant, since the rounded portion does not result in a stabbing pain.

The sensor shaft 41 has a blind hole 43 formed in the longitudinal extension of the sensor shaft 41 on the side opposite to the sensor head 42. The sensor shaft 41, the sensor head 42 and the blind hole 43 have the same center axis. The blind hole 43 has an inner diameter adjusted to the outer diameter of the shaft 21 of the electrode pin 2. In particular, the inner diameter of the blind hole 43 is almost equal to the outer diameter of the increased diameter portion 23 of the electrode pin 2.

In practical use, the sensor 4 is slid onto the distal end, i.e. the end portion of the electrode pin 2, provided with the rounded end 24, so that the extended diameter portion 23 of the electrode pin 2 enters into an elastic press fit with the blind hole 43 of the sensor 4. The sensor 4 slid onto the electrode pin 2 is shown in FIGS. 1C and 2B.

Ring 5:

The ring 5 is made of resin and has an inner diameter which is almost equal to the outer diameter of the cylinder sleeve 131 of the electrode holder bottom part 13. In practical use, the ring 5 is slid onto the cylinder sleeve 131 of the electrode holder bottom part 13. Thus, the cap 6 can be sandwiched between the ring 5 and the annular flange 132 of the electrode holder bottom part 13, when the cylinder sleeve 131 of the electrode holder bottom part 13 has been slid through a predefined electrode configuration hole of the cap 6. The ring 5 is shown in FIGS. 1A-1E.

Cap 6:

The cap 6 is made of an elastic material. It can be made of rubber, textile material or of synthetic rubber, such as neoprene, etc. The cap 6 is of such a size and form that it can be put onto and worn on the head of a test person. At predetermined positions, the cap 6 has circular openings in a cap body, in each of which an EEG electrode can be disposed. Every circular opening has an inner diameter which is, in a stretched state of the cap 6, slightly bigger than the outer diameter of the cylinder sleeve 131 of the electrode holder bottom part 13, as is seen in FIG. 1B. In a non-stretched state the inner circumference or periphery or circumferential surface of the circular opening preferably abuts against the outer circumference or periphery or circumferential surface of the cylinder sleeve 131.

Assembly of the EEG Electrode:

In its application, the EEG electrode is assembled as is shown in FIGS. 1A-1E. The electrode holder 12, 13 is assembled as previously described, wherein the ring 5 is put onto the outer diameter of the cylinder sleeve 131 of the electrode holder bottom part 13 between the wheel body 122 of the electrode holder upper part 12 and the annular flange 132 of the electrode holder bottom part 13. Then, the electrode housing 11 provided with the connection 3 and the electrode pin 2 is screwed into the electrode holder upper part 12 from the proximal side. Subsequently, the sensor 4 is slid onto the end of the electrode pin 2, projecting on the distal side.

Configuration of the EEG Electrode on the Cap 6:

The assembled EEG electrode is disposed on the cap 6 by being guided from the proximal side to a circular opening on the respective predetermined position. The elastic material of the cap 6 is pulled apart in such a way that the annular flange 132 having an outer diameter larger than the inner diameter of the circular opening of the cap 6, can pass through the circular opening. The EEG electrode is disposed in the circular opening of the cap 6 so that the inner circumference or periphery or circumferential surface of the circular opening of the cap 6 is disposed between the ring 5 and the annular flange 132 of the electrode holder bottom part 13. Then, the ring 5 is slid along the outer circumference or periphery or circumferential surface of the cylinder sleeve 131 towards the annular flange 132, so that the inner circumference or periphery or circumferential surface of the circular opening of the cap 6 is clamped between the ring 5 and the annular flange 132 of the electrode holder bottom part 13, as is seen in FIG. 1B.

Figure 1E:
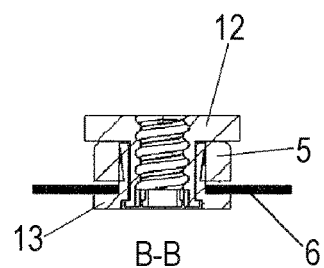
FIG. 1E shows a sectional view of the EEG electrode of FIG. 1D along the line B-B.

It is also possible to first place the electrode holder 12, 13 including the ring 5 on the cap 6, as is seen in FIG. 1E, and then screw the electrode housing 11 into the electrode holder 12, 13.

Application of the EEG Electrode:

The cap 6 provided with a sufficient amount of EEG electrodes is put on by the test person. The respective sensor head 42 is to be in contact with the test person's scalp. If there is no sufficient contact between a sensor 4 of an EEG electrode and the test person's scalp, the test person or the treating person grabs the wheel body 122 of the EEG electrode in question and turns the wheel body 122 in a clockwise direction. This makes the electrode holder upper part 12 rotate relative to the electrode holder bottom part 13, the ring 5 and the cap 6, but also relative to the electrode housing 11. During the clockwise screwing movement of the wheel body 122, the electrode housing 11 is steplessly moved in the axial direction relative to the electrode holder 12, 13 in the distal direction. Thus, the sensor head 42 approaches the test person's scalp. The test person stops the screwing movement of the wheel body 122 when a sufficient contact between the sensor 4 and the scalp is achieved. If the contact between the sensor 4 and the scalp is too close and the test person feels an uncomfortable pressure of the sensor 4, the test person appropriately turns the wheel body 122 in a counterclockwise direction and in doing so, the sensor head 42 moves away from the scalp. The radial orientation of the electrode housing 11 does not change during the screwing movement of the wheel body 122.

Effects and Advantages of the Invention

The relative displacement of the electrode housing 11 including the electrode pin 2 and the sensor 4, in relation to the electrode holder 12, 13, results in an individually adjustable axial length of every single EEG electrode.

The screwing movement of the electrode housing 11 relative to the electrode holder 12, 13 ensures a realization of a stepless axial displacement of the electrode housing 11 including the electrode pin 2 and the sensor 4, relative to the electrode holder 12, 13 and thus to the cap 6. Hence, in practical use, a sensor 4 can be steplessly displaced relative to the scalp.

A stepless axial displacement of the sensor 4 relative to the cap 6 is superior to a construction where a sensor can be displaced relative to the cap by a spring. A simple, linear spring follows the equation $F=k*x$ (F=spring force, k=spring constant, x=deflection). Through the use of such a spring it can be achieved that a variable distance (i.e. a variable deflection x) is bridged, so that the sensor always touches the scalp. However, it is a disadvantage that, when the deflection x is variable, this always takes place with different forces F. According to the present invention, an EEG electrode can be disposed on any particular position on the head with an arbitrarily adjustable force.

In addition, sensors 4 of different lengths can be used on the electrode pin 2. Thereby, the individual adjustability of the axial length of every individual EEG electrode can be even further improved.

The EEG electrode according to the invention can ideally be used as a dry electrode. The rounded sensor head 42 offers a relatively large surface and causes a relatively small contact pressure on the test person's skin. Thus, on one hand, a stable mechanical and electrical contact between the EEG electrode according to the invention and the scalp can be established. On the other hand, uncomfortable pressure on the scalp can be avoided while the contact pressure is still sufficient.

Since the radial orientation of the electrode housing 11 does not change during the screwing movement of the wheel body 122, the orientation of the connection 3 also remains unchanged during the stepless displacement of the sensor 4 relative to the scalp. Thus, cables provided between the EEG electrode and a measuring apparatus are not twisted during the screwing movement of the wheel body 122.

If, in practical use, the test person wants to increase the contact between a sensor 4 and his/her scalp, the test person or the treating person grabs the wheel body 122 of the electrode in question and turns the wheel body 122 in the clockwise direction. The specific construction of the EEG electrode and, in particular, the use of the left-hand thread ensure that the test person can intuitively perform the screwing movement in a way he/she knows from screwing movements performed in everyday life.

Alternatives:

In the embodiment of the invention the EEG electrode can be used on the scalp of the test person by using the cap 6. The principle of the invention is not limited thereto. The EEG electrode according to the invention can be applied on any point of the test person's skin if an appropriate holder is used. This means that areas of the skin other than only the scalp can also be used for acquiring electrophysiological signals.

In the embodiment of the invention it is made possible that the electrode housing 11 is steplessly axially displaced relative to the electrode holder 12, 13 through a thread by using a screwing movement. Alternatively, the through opening 121 and the cylindrical extension 111 need not have a thread in order to realize a stepless displacing movement of the electrode housing 11 relative to the electrode holder 12, 13. An arresting device provided on the through opening 121 or the cylindrical extension 111 ensures the desired relative positioning of the electrode housing 11 relative to the electrode holder 12, 13.

The cap 6 does not have to be made of an elastic material. The EEG electrode according to the invention can also be used in a cap made of a non-elastic material.

The advantage of the construction including a left-hand thread is explained above. The principle of the invention can also be applied to an EEG electrode where the through opening 121 and the cylindrical extension 111 are provided with a right-hand thread.

The sensors 4 can be omitted. The principle of the invention is also applicable if the electrode pin 2 also takes on the function of the sensor 4. Then, an electrode pin 2 including a sensor head similar to the sensor head 42 can be disposed in the electrode housing 11.

In the embodiment of the invention, the sensor 4 is plugged onto the electrode pin 2. In an alternative, an electrode pin having a sleeve-like end into which a pin-like shaped sensor is inserted can be used.

The invention claimed is:

1. A sensor device suitable for receiving and transmitting signals and for placement on a test person's head, the sensor device comprising:
   a sensor device holder having an axial through opening;
   a sensor device housing disposed in said axial through opening so as to be steplessly axially displaceable, said sensor device housing having a distal side and a proximal side;
   said sensor device housing having a radial orientation being maintained upon said sensor device housing being axially displaced relative to said sensor device holder;
   a signal pin disposed on said distal side of said sensor device housing for receiving a signal;
   a connection disposed on said proximal side of said sensor device housing for signal transmission of a signal received by said signal pin;
   said sensor device holder formed of an assembly consisting of a proximal electrode holder upper part and a distal sensor device holder bottom part, said upper part including said axial through opening;
   said upper part being rotatable relative to said bottom part in the bottom part, and said upper part not moving axially relative to said bottom part;
   said bottom part configured for anchorage in a cap to be worn on the test person's head.

2. The sensor device according to claim 1, wherein:
   said axial through opening of said sensor device holder has an inner circumferential surface with an inner thread;

said sensor device housing has an outer circumferential surface with an outer thread; and said sensor device housing is steplessly axially displaceable in said sensor device holder by using a screwing movement.

3. The sensor device according to claim 2, wherein said inner thread of said sensor device holder and said outer thread of said sensor device housing are constructed as left-hand threads, and said screwing movement of said sensor device housing into said sensor device holder is effected in a clockwise direction.

4. The sensor device according to claim 1, wherein:
said signal pin has a distal side;
a sensor for acquiring a signal is detachably attached on said distal side of said signal pin;
said sensor forms an elongation of said signal pin;
said sensor has a distal side; and
said sensor has a flattened contact surface on said distal side of said sensor for contact with the test person.

5. The sensor device according to claim 4, wherein said sensor is one of a plurality of sensors of different lengths to be detachably attached on said distal side of said signal pin.

6. The sensor device according to claim 1, wherein:
said sensor device holder upper part includes a knurled wheel provided with an outer circumferential surface having a knurl.

7. The sensor device according to claim 1, wherein said connection for signal transmission is a sheer conductor or a circuit board having at least one of an amplifier or a preamplifier or A/D converters or optical fibers or a capacitive signal coupling.

8. The sensor device according to claim 1, wherein the sensor device is an EEG electrode suitable for receiving and transmitting EEG signals.

9. A cap, comprising:
a plurality of sensor devices according to claim 1;
a cap body having predefined openings formed therein;
said sensor device holder of each respective sensor device being disposed in a respective one of said predefined openings in said cap body, permitting said sensor device housing to be operated from a side of said cap body opposite to said signal pins for a stepless axial displacement of said sensor device housing relative to said sensor device holder.

10. The cap according to claim 9, wherein said cap body is made of an elastic material.

11. The cap according to claim 9, wherein said cap body is made of a non-elastic material.

* * * * *